US007579438B2

(12) United States Patent
Mora et al.

(10) Patent No.: US 7,579,438 B2
(45) Date of Patent: Aug. 25, 2009

(54) USE OF THE GENE NCSAG4 FOR THE DIAGNOSIS AND PREVENTION OF NEOSPOROSIS AND AS A MARKER FOR ANALYSIS OF THE PATHOGENESIS

(75) Inventors: Luis Miguel Ortega Mora, Madrid (ES); Aurora Fernandez Garcia, Madrid (ES)

(73) Assignee: Universidad Complutense De Madrid, Madrid (ES)

( * ) Notice: Subject to any disclaimer, the term of this patent is extended or adjusted under 35 U.S.C. 154(b) by 0 days.

(21) Appl. No.: 10/581,810

(22) PCT Filed: Nov. 26, 2004

(86) PCT No.: PCT/ES2004/000529

§ 371 (c)(1),
(2), (4) Date: Mar. 12, 2007

(87) PCT Pub. No.: WO2005/053505

PCT Pub. Date: Jun. 16, 2005

(65) Prior Publication Data

US 2007/0275018 A1 Nov. 29, 2007

(30) Foreign Application Priority Data

Dec. 4, 2003 (ES) ............................... 200302869

(51) Int. Cl.
*C07K 14/00* (2006.01)
(52) U.S. Cl. ..................................... 530/350; 435/975
(58) Field of Classification Search .................. 530/350
See application file for complete search history.

(56) References Cited

U.S. PATENT DOCUMENTS

| 6,436,410 | B1 * | 8/2002 | Krishnan et al. ......... 424/265.1 |
| 2003/0180785 | A1 | 9/2003 | Krishnan et al. |
| 2005/0186227 | A1 * | 8/2005 | Choromanski et al. ... 424/269.1 |

FOREIGN PATENT DOCUMENTS

EP 1033405 A2 * 9/2000

OTHER PUBLICATIONS

Innes et al (Trends in Parasitology Vol. 18 (11) pp. 497-504, 2002).*
Alvarez-Garcia, G. et al. (2002) "Pattern of recognition of *Neospora caninum* tachyzoite antigens by naturally infected pregnant cattle and aborted foetuses" *Vet. Parasitol.* 107:15-27.
Alvarez-Garcia, G. et al. (2003) "Influence of age and purpose for testing on the cut-off selection of serological methods in bovine neosporosis" *Vet. Res.* 34:341-352.
Anderson, M. et al. (2000) "Neosporosis in cattle" *Animal Reproduct. Sci.* 60-61:417-431.
Andrianarivo, A. et al. (1999) "Immunogenicity of a killed whole *Neospora caninum* tachyzoite preparation formulated with different adjuvants" *Int. J. Parasitol.* 29:1613-1625.

Asai, T. et al. (1998) "*Neospora caninum*: tachyzoites express a potent type-1 nucleoside triphosphate hydrolase, but lack nucleoside disphosphate hydrolase activity" *Exp. Parasitol.* 90:277-285.
Atkinson, R. et al. (1999) "Comparison of the biological characteristics of two isolates of *Neospora caninum*" *Parasitology* 118:363-370.
Barr, B. et al. (1992) "Neospora-like protozoal infections associated with abortion in goats" *J. Vet. Diagn. Invest.* 4:365-367.
Baszler, T. et al. (1996) "Serological diagnosis of bovine neosporosis by *Neospora caninum* monoclonal antibody-based competitive inhibition enzyme-linked immunosorbent assay" *J. Clin. Microbiol.* 34:1423-1428.
Bjorkman, C. et al. (1996) "Neospora species infection in a herd of diary cattle" *JAVMA* 208:1441-1444.
Bohne, W. et al. (1996) "Bradyzoite-specific genes" *Curr. Top. Microbiol. Immunol.* 219:81-91.
Buxton, D. et al. (2002) "The comparative pathogenesis of neosporosis" *Trends Parasitol.* 18:546-552.
Cannas, A. et al. (2003) "Reduced cerebral infection of *Neospora caninum*-infected mice after vaccination with recombinant microneme protein NCMIC3 and ribi adjuvant" *J. Parasitol.* 89:44-50.
Cultrera, R. et al. (2002) "Efficacy of a novel reverse transcriptase-polymerase chain reaction (RT-PCR) for detecting *Toxoplasma gondii* bradyzoite gene expression in human clinical specimens" *Mol. Cell. Probes* 16:31-39.
Davison, H. et al. (1999) "Estimation of vertical and horizontal transmission parameters of *Neospora caninum* infections in dairy cattle" *Int. J. Parasitol.* 29:1683-16889.
Dubey, J. et al. (1990) "Congenital *Neospora caninum* infection in a calf with spinal cord anomaly" *JAVMA* 197:1043-1044.
Dubey, J. et al. (1996) "A review of *Neospora caninum* and neosporosis" *Vet. Parasitol.* 67:1-59.
Dubey, J. et al. (1988) "Newly recognized fatal protozoan disease of dogs" *JAVMA* 192:1269-1285.
Ferre, I. et al. (2003) "Recent advances in the diagnosis of bovine neosporosis" Departamento de Sanidad Animal, Facultad de Veterinaria, Universidad Complutense de Madrid, 10 pp.
Fuchs, N. et al. (1998) "Differential expression of cell surface- and dense granule-associated *Neospora caninum* proteins in tachyzoites and bradyzoites" *J. Parasitol.* 84:753-758.
Gerber, L. et al. (1992) "Phosphatidylinositol glycan (PI-G) anchored membrane proteins" *J. Biol. Chem.* 267:12168-12173.
Kobayashi, Y. et al. (2001) "Naturally-occurring *Neospora caninum* infection in an adult sheep and her twin fetuses" *J. Parasitol.* 87:434-436.

(Continued)

*Primary Examiner*—Mark Navarro
(74) *Attorney, Agent, or Firm*—Knobbe Martens Olsen & Bear LLP

(57) ABSTRACT

The invention relates to gene NcSAG4, the RNA messenger of said gene, the oligonucleotides designed based on the nucleotide sequence thereof or any of the fragments of same, and to protein NcSAG4 encoded thereby, or any of the recombinant forms of same, expression vectors, and host cells containing same, for the purpose of diagnosis and vaccination for the prevention of neosporosis. The invention also relates to the use thereof as a specific marker of the *N. caninum* bradyzoite stage, for the analysis of the pathogenesis or the effectiveness of vaccines against the establishment of a chronic infection in the intermediate host.

6 Claims, 7 Drawing Sheets

OTHER PUBLICATIONS

Laemmli, U. (1970) "Cleavage of structural proteins during the assembly of the head of bacteriophage T4" *Nature* 227:680-685.

Lally, N. et al. (1996) "Evaluation of two *Neospora caninum* recombinant antigens for sue in an enzyme-linked immunosorbent assay for the diagnosis of bovine neosporosis" *Clin. Diag. Laboratory Immunol.* 3:275-279.

Liddell, S. et al. (1999) "A competitive PCR assay for quantitative detection of *Neospora caninum*" *Int J. Parasitol.* 29:1583-1587.

Liddell, S. et al. (2003) "Immunization of mice with plasmid dna coding for NcGRA7 or NcsHSP33 confers partial protection against vertical transmission of *Neospora caninum*" *J. Parasitol.* 89:496-500.

Lindsay, D. et al. (1989) "Evaluation of anti-coccidial drugs' inhibition of *Neospora caninum* development in cell cultures" *J. Parasitol.* 75:990-992.

Lindsay, D. et al. (1999) "Characterization of temperature-sensitive strains of *Neospora caninum* in mice" *J. Parasitol.* 85:64-67.

Louie, K. et al. (1997) "Cloning and Characterization of two recombinant neospora protein fragments and their use in serodiagnosis of bovine neosporosis" *Clin. Diagn. Laboratory Immunol.* 4:692-699.

Louie, K. et al. (1999) "Characterization of a cDNA encoding a subtilisin-like serine protease (NC-p65) of *Neospora caninum*" *Mol. Biochem. Parasitol.* 103: 211-223.

Louie, K. et al. (2002) "Characterization of *Neospora caninum* protease, NcSUB1 (NC-p65), with rabbit anti-N54" *J. Parasitol.* 88: 1113-1119.

Lyons, R. et al. (2002) "*Toxoplasma gondii* tachyzoite-bradyzoite interconversion" *Trends Parasitol.* 18:198-201.

Naguleswaran, A. et al. (2001) "*Neospora caninum* microneme protein NcMIC3: secretion, subcellular localization, and functional involvement in host cell interaction" *Infect. Immun.* 69:6483-6494.

Odberg-Ferragut, C. et al. (1996) "Molecular cloning of the *Toxoplasma gondii* sag4 gene encoding an 18 kDa bradyzoite specific surface protein" *Mol. Biochem. Parasitol.* 82:237-244.

Pare, J. et al. (1996) "Congenital *Neospora caninum* infection in diary cattle and associated calfhood mortality" *Can. J. Vet. Res.* 60:133-139.

Pereira-Bueno, J. et al. (2003) "Evaluation by different diagnostic techniques of bovine abortion associated with *Neospora caninum* in Spain" *Vet. Parasitol.* 111:143-152.

Peters, M. et al. (2001) "Immunohistochemical and ultrastructural evidence for *Neospora caninum* tissue cysts in skeletal muscles of naturally infected dogs and cattle" *Int. J. Parasitol.* 31:1144-1148.

Risco-Castillo, V. et al. (2004) "comparative analysis of stress agents in a simplified in vitro system of *Neospora caninum* bradyzoite production" *J. Parasitol.* 90:466-470.

Schares, G. et al. (1998) "The efficiency of vertical transmission of *Neospora caninum* in diary cattle analysed by serological techniques" *Vet. Parasitol.* 80:87-98.

Schares, G. et al. (1999) "*Neospora caninum*: identification of 19-, 38-, and 40-kDa surface antigens and a 33-kDa dense granule antigen using monoclonal antibodies" *Exp. Parasitol.* 92:109-119.

Sonda, S. et al. (2000) "Molecular characterization of a novel microneme antigen in *Neospora caninum*" *Mol. Biochem. Parasitol.* 108:39-51.

Thilsted, J.P. et al. (1989) "Neosporosis-like abortions in a herd of dairy cattle" *J. Vet. Diagn. Invest.* 1:205-209.

Thurmond, M. (1995) "Strategies to control neospora infection in cattle" *The Bovine Practitioner* 29:60-63.

Tomavo, S. et al. (1991) "Characterization of bradyzoite-specific antigens of *Toxoplasma gondii*" *Infect. Immun.* 59:3750-3753.

Trees, A.J. et al. (1999) "Towards evaluating the economic impact of bovine neosporosis" *Int. J. Parasitol.* 29:1195-1200.

Wouda, W. et al. (1998) "Abortion risk in progeny of cows after a *Neospora caninum* epidemic" *Theriogenology* 49:1311-1316.

Burg, J.L. et al. 1988 "Molecular analysis of the gene encoding the major surface antigen of *Toxoplasma gondii*" *J Immunol* 141:3584-3591.

Cerede, O. et al. 2001 "Identification and molecular characterization of a *Toxoplasma gondii* mocroneme" *Ann Pharm Fr* 59:292-296.

Fernandez-Garcia, A. et al. 2006 "Identification and molecular cloning of the *Neospora caninum* SAG4 gene specifically expressed at bradyzoite stage" *Molec Biochem Parasitol* 146:89-97.

Holec, L. et al. 2008 "*Toxoplasma gondii*: Enzyme-linked immunosorbent assay using different fragments of recombinant microneme protein 1 (MIC1) for detection of immunoglobulin G antibodies" *Experimental Parasitology* 119:1-6.

Yano, A. et al. 1997 "Correlation between direct binding ability of synthetic *T. gondii* SAG1 peptides to HLA-A2 measured by a sensor for surface plasmon resonance and antigenicity of the peptides for *T. gondii*-infected cell-specific CTL" *Biochem and Biophys Res Comm* 236:257-261.

* cited by examiner

Panel A

Panel B

Panel C pRNcSAG4 →

SEQUENCE LISTING

```
<160> NUMBER OF SEQ ID NOS: 15

<210> SEQ ID NO 1
<211> LENGTH: 23
<212> TYPE: DNA
<213> ORGANISM: Neospora caninum
<220> FEATURE:
<221> NAME/KEY: modified_base
<222> LOCATION: 6
<223> OTHER INFORMATION: I

<400> SEQUENCE: 1
tggacntayg ayttyaaraa rgc                                              23

<210> SEQ ID NO 2
<211> LENGTH: 23
<212> TYPE: DNA
<213> ORGANISM: Neospora caninum
<220> FEATURE:
<221> NAME/KEY: modified_base
<222> LOCATION: 12, 15, 18, 21
<223> OTHER INFORMATION: I

<400> SEQUENCE: 2
aaraargara tnatnacncc ngg                                              23

<210> SEQ ID NO 3
<211> LENGTH: 23
<212> TYPE: DNA
<213> ORGANISM: Neospora caninum
<220> FEATURE:
<221> NAME/KEY: modified_base
<222> LOCATION: 3
<223> OTHER INFORMATION: I

<400> SEQUENCE: 3
acnggytcrt cyttrcartg rtc                                              23

<210> SEQ ID NO 4
<211> LENGTH: 24
<212> TYPE: DNA
<213> ORGANISM: Neospora caninum
<220> FEATURE:
<221> NAME/KEY: modified_base
<222> LOCATION: 22
<223> OTHER INFORMATION: I
<220> FEATURE:
<221> NAME/KEY: misc_feature
<222> LOCATION: 7
<223> OTHER INFORMATION: n = A,T,C or G

<400> SEQUENCE: 4
rtcyttnacy ttraarcara angg                                             24

<210> SEQ ID NO 5
<211> LENGTH: 20
<212> TYPE: DNA
<213> ORGANISM: Neospora caninum

<400> SEQUENCE: 5
ccgacgaagc cctgagaact                                                  20

<210> SEQ ID NO 6
<211> LENGTH: 19
<212> TYPE: DNA
<213> ORGANISM: Neospora caninum
```

<400> SEQUENCE: 6
tgtcgcctgt tgggttgta                                                    19

<210> SEQ ID NO 7
<211> LENGTH: 24
<212> TYPE: DNA
<213> ORGANISM: Neospora caninum

<400> SEQUENCE: 7
gaaacaagaa aagagactat ctca                                              24

<210> SEQ ID NO 8
<211> LENGTH: 20
<212> TYPE: DNA
<213> ORGANISM: Neospora caninum

<400> SEQUENCE: 8
ccaggtgaga gtgtttcgat                                                   20

<210> SEQ ID NO 9
<211> LENGTH: 601
<212> TYPE: DNA
<213> ORGANISM: Neospora caninum
<220> FEATURE:
<221> NAME/KEY: CDS
<222> LOCATION: (48)...(568)

<400> SEQUENCE: 9
ggcaacacgt cgcagcgtac tctcatcttt ttcgtgggtt tgcagcc atg gag aaa         56
                                                    Met Glu Lys
                                                     1 agc gcc ttc ttt ccc agg gtg gtg ctc tgt ttc gtc gta gtt ttg tcc        104
Ser Ala Phe Phe Pro Arg Val Val Leu Cys Phe Val Val Val Leu Ser
      5                  10                  15 gcg tgc tcg gcg tgg cga gtg gaa ggg aag aac tgg tcg tac gat ttc        152
Ala Cys Ser Ala Trp Arg Val Glu Gly Lys Asn Trp Ser Tyr Asp Phe
 20                  25                  30                  35 aag aag ccg ctg gac agc gat gaa aca aga aaa gag act atc tca cca        200
Lys Lys Pro Leu Asp Ser Asp Glu Thr Arg Lys Glu Thr Ile Ser Pro
                 40                  45                  50 ggt gag agt gtt tcg ata caa aat tct ggg agc att acg ctg gcg tac        248
Gly Glu Ser Val Ser Ile Gln Asn Ser Gly Ser Ile Thr Leu Ala Tyr
             55                  60                  65 aac cca aca ggc gac aca caa gtt ctc agg gct tcg tcg gga gac agc        296
Asn Pro Thr Gly Asp Thr Gln Val Leu Arg Ala Ser Ser Gly Asp Ser
         70                  75                  80 tgc agg gat gag cca atc gaa ctt gcg act tta ttc cca gca gcc acg        344
Cys Arg Asp Glu Pro Ile Glu Leu Ala Thr Leu Phe Pro Ala Ala Thr
     85                  90                  95 ccg gcg ccc acg tgg atg caa act ggt agc acg aga acc tta gcg ttt        392
Pro Ala Pro Thr Trp Met Gln Thr Gly Ser Thr Arg Thr Leu Ala Phe
100                 105                 110                 115 cct acc aac gca gta ccc gcg aag cag acc acg ccg ttc tgt ttt aaa        440
Pro Thr Asn Ala Val Pro Ala Lys Gln Thr Thr Pro Phe Cys Phe Lys
                 120                 125                 130 gtc acg gat acg cag aag aac aaa act ctg aca gcg ata atc aag gtc        488
Val Thr Asp Thr Gln Lys Asn Lys Thr Leu Thr Ala Ile Ile Lys Val
             135                 140                 145 gcc ggt gcc caa ggc ttg tct gct gct ctg ggg gtc tcc att gga ata        536
Ala Gly Ala Gln Gly Leu Ser Ala Ala Leu Gly Val Ser Ile Gly Ile
         150                 155                 160

```
cca gct ctt gct ttt gca ctg agt tcg ata ta agggcatgca aacgaataaa      588
Pro Ala Leu Ala Phe Ala Leu Ser Ser Ile
    165                 170 tgaggcgact gat                                                        601
```

<210> SEQ ID NO 10
<211> LENGTH: 173
<212> TYPE: PRT
<213> ORGANISM: Neospora caninum

<400> SEQUENCE: 10

```
Met Glu Lys Ser Ala Phe Phe Pro Arg Val Val Cys Phe Val Val
 1               5                  10                  15

Val Leu Ser Ala Cys Ser Ala Trp Arg Val Glu Gly Lys Asn Trp Ser
            20                  25                  30

Tyr Asp Phe Lys Lys Pro Leu Asp Ser Asp Glu Thr Arg Lys Glu Thr
            35                  40                  45

Ile Ser Pro Gly Glu Ser Val Ser Ile Gln Asn Ser Gly Ser Ile Thr
        50                  55                  60

Leu Ala Tyr Asn Pro Thr Gly Asp Thr Gln Val Leu Arg Ala Ser Ser
65                  70                  75                  80

Gly Asp Ser Cys Arg Asp Glu Pro Ile Glu Leu Ala Thr Leu Phe Pro
                85                  90                  95

Ala Ala Thr Pro Ala Pro Thr Trp Met Gln Thr Gly Ser Thr Arg Thr
            100                 105                 110

Leu Ala Phe Pro Thr Asn Ala Val Pro Ala Lys Gln Thr Thr Pro Phe
        115                 120                 125

Cys Phe Lys Val Thr Asp Thr Gln Lys Asn Lys Thr Leu Thr Ala Ile
    130                 135                 140

Ile Lys Val Ala Gly Ala Gln Gly Leu Ser Ala Ala Leu Gly Val Ser
145                 150                 155                 160

Ile Gly Ile Pro Ala Leu Ala Phe Ala Leu Ser Ser Ile
                165                 170
```

<210> SEQ ID NO 11
<211> LENGTH: 26
<212> TYPE: DNA
<213> ORGANISM: Neospora caninum

<400> SEQUENCE: 11

```
gccaggatcc atgagaaaaa gcgcct                                          26
```

<210> SEQ ID NO 12
<211> LENGTH: 31
<212> TYPE: DNA
<213> ORGANISM: Neospora caninum

<400> SEQUENCE: 12

```
ttcgaattcc ttatatcgaa ctcagtgcaa a                                    31
```

<210> SEQ ID NO 13
<211> LENGTH: 28
<212> TYPE: DNA
<213> ORGANISM: Neospora caninum

<400> SEQUENCE: 13

```
ttatggatcc ggaagaactg gtcgtacg                                        28
```

```
<210> SEQ ID NO 14
<211> LENGTH: 30
<212> TYPE: DNA
<213> ORGANISM: Neospora caninum

<400> SEQUENCE: 14
tttgaattcc ttaggcgacc ttgattatcg                                     30

<210> SEQ ID NO 15
<211> LENGTH: 155
<212> TYPE: PRT
<213> ORGANISM: Neospora caninum

<400> SEQUENCE: 15
```

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Ile Arg Lys Asn Trp Ser Tyr Asp Phe Lys Lys Pro Leu Asp
        35                  40                  45

Ser Asp Glu Thr Arg Lys Glu Thr Ile Ser Pro Gly Glu Ser Val Ser
    50                  55                  60

Ile Gln Asn Ser Gly Ser Ile Thr Leu Ala Tyr Asn Pro Thr Gly Asp
65                  70                  75                  80

Thr Gln Val Leu Arg Ala Ser Ser Gly Asp Ser Cys Arg Asp Glu Pro
            85                  90                  95

Ile Glu Leu Ala Thr Leu Phe Pro Ala Ala Thr Pro Ala Pro Thr Trp
            100                 105                 110

Met Gln Thr Gly Ser Thr Arg Thr Leu Ala Pro Thr Asn Ala Val Pro
            115                 120                 125

Ala Lys Gln Thr Thr Pro Phe Cys Phe Lys Val Thr Asp Thr Gln Lys
            130                 135                 140

Asn Lys Thr Leu Thr Ala Ile Ile Lys Val Ala
145                 150                 155

USE OF THE GENE NCSAG4 FOR THE DIAGNOSIS AND PREVENTION OF NEOSPOROSIS AND AS A MARKER FOR ANALYSIS OF THE PATHOGENESIS

Related Applications

This application is a US National Phase of International Application No.: PCT/ES2004/000529, filed Nov. 26, 2004, designating the US and published not in English on Jun. 16, 2005 as WO 2005/053505, which claims the benefit of Spanish Patent Application No.: P200302869, filed Dec. 4, 2003.

OBJECT OF THE INVENTION

The invention is established in the field of animal health and relates, as expressed in the heading of this descriptive report, to the diagnosis, analysis of the pathogenesis and prevention of the disease caused by the protozoan parasite *Neospora caninum*. The invention is more specifically related to the polynucleotide molecule corresponding to gene NcSAG4 of *N. caninum*, its RNA messenger and to the antigen encoded thereby, NcSAG4, which is a specific protein of the bradyzoite stage as well as oligonucleotides, recombinant vectors, transformed host cells, and proteins expressed recombinantly, the use of same as reagents for the diagnosis of the disease, its application to the development of molecular techniques that allow for studying the pathogenesis of the disease, in addition to its value for producing vaccines.

BACKGROUND

Neosporosis

*N. caninum* is a protozoan parasite belonging to the phylum Apicomplexa that includes other significant parasitic pathogens such as *Toxoplasma gondii* which is closely related to it. *N. caninum* has been described since 1989 as an agent causing abortion and neonatal mortality in cattle (Thilsted and Dubey. 1989. J. Vet. Diagn. Invest. 1, 205-209), though it can infect a wide range of mammal species (Buxton et al. 2002, Trends Parasitol. 18, 546-552).

Bovine neosporosis is considered to be a parasitic disease of worldwide distribution and one of the most common causes of reproduction failure in the various countries where it was studied (Trees et al. 1999. Int. J. Parasitol. 29, 1195-1200; Anderson et al. 2000, Anim. Reprod. Sci. 60-61, 417-431), including Spain (González et al. 1999. Vet. Rec. 144, 145-150; Pereira-Bueno et al. 2003. Vet. Parasitol. 111, 143-152). The most important clinical manifestation of the infection in pregnant females is abortion that generally occurs between the third and ninth month of pregnancy, and most commonly around 5-6 months. Calves affected that are born alive can show neuromuscular problems, with the first clinical signs appearing at 4-5 days post-delivery, though they can be delayed for up to two weeks. However, most commonly, healthy calves are born, though chronically infected (Dubey and Lindsay, 1999. Vet. Parasitol. 67, 1-59). Furthermore, neosporosis can affect dogs, their definitive host, where it causes polymyositis, encephalitis, paralysis and can cause death (Lindsay and Dubey, 1989. J. Parasitol. 75, 163-165; Buxton et al. 2002. Trends Parasitol. 18, 546-552).

Like *T. gondii*, the life cycle of *N. caninum* encompasses three stages. Sporozoites, which infect the intermediate host by intake of the oocysts eliminated by the definitive host. On the other hand, tachyzoites, the fast replication form, responsible for the acute stage of the infection, with the role of dissemination through the host tissues. This process ends when the host develops immunity and a chronic phase is then established, with slow multiplication of the parasite, and formation of tissue cysts with bradyzoites inside, that have been observed in both nervous tissue of several species with natural and experimental infections (Dubey et al., 1988, J. Am. Vet. Med. Assoc. 193, 1259-1263; Dubey et al. 1990. J. Am. Vet. Med. Assoc. 197: 1043-1044; Barr et al. 1992. J. Vet Diagn. Invest. 4, 365-367; Kobayashi et al. 2001. J. Parasitol. 87:434-436) and in the skeletal muscle tissue of dog and cow in natural infections (Peters et al. 2001. Int. J. Parasitol. 31, 1144-1148). These bradyzoites are latent in the cysts of tissues until reactivation (Antony and Williamson. 2001. New Zeal. Vet. J. 49, 42-47; Buxton et al. 2002. Trends Parasitol. 18, 546-552). The mechanisms underlying in the turning of the tachyzoite into bradyzoite and vice versa in parasites of the Apicomplexa group, such as *T. gondii* or *N. caninum*, are not known today, but it has been suggested that the immune response can be influencing the latency and reactivation of the infection in animals with chronic infection (Lyons, et al., 2002, Trends Parasitol. 18, 198-201).

With regard to the transmission of the disease, the most recent studies suggest the relatively low importance of postnatal transmission and refer to the persistence, throughout life, of the congenital infection (Davison et al. 1999. Int. J. Parasitol. 29, 1683-1689; Hietala and Thurmond. 1999. Int. J. Parasitol. 29. 1669-1676). Congenital transmission plays a major role with percentages ranging between 50% and 95% (Wouda et al. 1998. Theriogenology 49, 1311-1316; Pereira-Bueno et al. 2000. in: Hemphill and Gottstein (Eds.) Int. J. Parasitol. 30, 906-909) and appears to play a highly significant role in the dissemination and maintenance of the disease (Björkman et al. 1996. J. Am. Vet. Med. Assoc. 208, 1441-1444; Paré et al. 1996 Can. J. Vet. Res. 60, 133-139; Anderson et al. 1997. J. Am. Vet. Med. Assoc. 210, 1169-1172; Schares et al. 1998. Vet. Parasitol. 80, 87-98).

*N. caninum* Antigens

With regard to the comparison of the antigen composition between the tachyzoite and the bradyzoite of *N. caninum*, very limited information is available to date, as only one study has been performed that identified specific antigens of the tachyzoite or shared by both stages (Fuchs et al. 1998. J. Parasitol. 84, 753-758), which is in contrast to studies performed in *T. gondii*, where several specific stage antigens are identified and characterised. The *N. caninum* antigens include two surface proteins, NcSAG1 (Hemphill et al. 1997, Parasitology, 115, 371-380), specific of tachyzoite, whose gene was cloned by Howe et al. (1998. Infect. Immun, 66, 5322-5328) and NcSRS2 (Hemphill et al. 1996, Parasitol. Res. 82, 497-504), expressed jointly in tachyzoites and bradyzoites. Both surface proteins of *N. caninum* have been recently tested as subunit vaccines in a murine model (Cannas et al. 2003a. Parasitology 126 (Pt. 4), 303-312). Two microneme proteins, NcMIC3 (Sonda et al. 2000. Mol. Biochem. Parasitol 108, 39-51) and NcMIC1 (Keller et al. 2002. Infect. Immun. 70, 3187-3198), expressed in both stages of the parasite have been recently identified. Furthermore, two sequences of *Neospora* called NcMIC10 and NcMIC11 have been included in the gene bank, that could code two proteins of microneme, as their sequences are highly comparable to sequences coding the proteins of *T. gondii* TgMIC10 and TgMIC11, respectively. Other genes that have been cloned are NcGRA6 and NcGRA7, which code proteins of dense granules of the tachyzoite of *N. caninum*, based on which an ELISA was developed for the diagnosis of the disease (Lally et al. 1996. Clin. Diagn. Lab. Immunol. 3, 275-279). In addition to these proteins, others from dense granules of 29 and 67 kDa, called NcNTPase-I (Asai et al. 1998 Exp. Parasitol. 90, 277-285) and NcGRA2 (Ellis et al. 2000. Parasitology 120 (Pt 4), 383-390), respectively, have been identified and characterised. On the other hand, protein NcMIC3, located in the micronemes of intracellular tachyzoites (Naguleswaran et al. 2001. Infect. Immun. 69, 6483-6494), which gene has been cloned, was expressed as recombinant protein to be used for vaccination purposes (Cannas et al. 2003b. J. Parasitol. 89 (pt. 1) 44-50).

Finally, NcSUB1 is the only cloned gene of *N. caninum*, that expresses an enzyme. NcSUB1 is a serin-protease of 65 kDa (Louie and Conrad. 1999. Mol. Biochem. Parasitol. 103, 211-223; Louie et al. 2002. J. Parasitol. 88, 1113-1119), located in the micronemes of the tachyzoite, which shows a high amino acid identity with the *T. gondii* protein called TgSUB1.

With regard to specific antigens of the bradyzoite of *Neospora*, none have been identified to date, due to the difficulty to obtain cysts with bradyzoites both in vitro and in vivo. However, in *T. gondii* specific bradyzoite antigens have been described, including a surface antigen (SAG4/p18) which is recognized by a monoclonal antibody (T83B1) directed against a protein of 18 kDa (Tomavo et al. 1991. Infect. Immun. 59, 3750-3753). The gene TgSAG4 encoding this protein in *T. gondii* has been cloned and characterised by Ödberg-Ferragut et al. (1996, Mol. Biochem. Parasitol. 83, 237-244).

The antigen TgSAG4 *T. gondii* is a membrane protein anchored by phosphatidylinositol glycans (PI-G). The detection of this specific antigen of the slow growth stage, associated with chronic infection by *T. gondii*, has a significant diagnostic value as recently shown by Cultrera et al. (2002, Mol. Cell. Probes 16, 31-39). These authors have developed an RT-PCR for the detection of infection by *T. gondi*, based on the detection of mRNA of the gene TgSAG4 in cerebrospinal fluid of AIDS patients, where *T. gondii* can cause fatal encephalopathy.

Diagnosis and Prevention of Neosporosis Therefore, since vertical transmission of the disease appears to be the best method of establishment of the disease persistently in exploitations and as neosporosis is one of the main causes of abortion and neonatal mortality in cattle, with the attendant economic losses, control must be mainly aimed at reducing the prevalence of the infection in farms, establishing selective measures for culling and replacement to reduce the number of infected animals.

The etiological diagnosis of abortion in cattle is complex and laborious. In cases where an etiological diagnosis is reached, more than 90% correspond to infectious and parasitic agents where *N. caninum* currently plays a major role. With regard to the diagnosis of infection by *N. caninum*, it is essential to perform a laboratory diagnosis to confirm the etiology of the abortion, where serological diagnosis techniques play a major role and provide initial information about the significance of the problem. In adults, the laboratory diagnosis is performed by the detection of specific serum antibodies, which is very useful to establish effective measures for the control of infection, as this type of studies provides highly valuable information about the distribution and frequency of infections in farms (herd seroprevalence) and the risk of abortion due to neosporosis in infected herds (intra-herd seroprevalence) (Thurmond and Hietala. 1995. Parasitol. 81, 364-367; Paré et al. 1996. Can. J. Vet. Res. 60, 133-139).

Therefore, improving the diagnosis is extremely important to accurately establish the health condition of the animals. With this regard, a number of studies have been performed with the aim of validating serological techniques currently used, clarifying some controversial issues, such as the selection of the cut-off point based on the age of the animal and the technique used (Alvarez-Garcia et al. 2003. Vet. Res. 34, 341-352).

As several diagnostic techniques are currently used for *N. caninum* (Ferre et al. 2003. Res. Adv. Microbiol. 3, 157-167), but none of them allow for distinguishing between a recent and a chronic infection, the identification of specific tachyzoite and bradyzoite antigens, respectively, allows the development of diagnostic techniques that provide more information about the future of the farm in terms of abortions and improve the control of the disease. The expression of these antigens as recombinant proteins and their use for the serological diagnosis of neosporosis provide a highly valuable novel tool. With this regard, diagnostic methods, such as ELISA, have been developed, based on several *N. caninum* proteins produced in different types of heterologous expression systems (Lally et al. 1996. Clin. Diagn. Lab. Immunol. 3, 275-279; Louis et al. 1997. Clin. Diagn. Lab. Immunol. 4(6), 692-699), but to date none based on specific bradyzoite antigens. Furthermore, the development of monoclonal antibodies and monospecific polyclonal sera against stage specific antigens are an alternative for the diagnosis by the development of a competition ELISA, such as that performed against a protein of 65 kDA of *N. caninum* tachyzoite (Baszler et al. 1996. J. Clin. Microbiol. 34(6), 1423-1428).

On the other hand, the pharmacological control of neosporosis in cattle is currently unfeasible, there is no experience in the pharmacological treatment of the disease in bovines and the data available are not encouraging. However, the high cost of a possible treatment, doilable are not encouraging. however, the high do uninnive for the diagnosis by the development the appearance of possible resistances and residues in meat or milk, limit chemotherapy as a control measure. Therefore, immunoprophylaxis should be added to the measures for managing the herd.

With this regard, investigations performed recently for the preparation of a vaccine against *N. caninum* have included the assessment of dead vaccines with variable results, finding some protection against vertical transmission in a murine model (Liddell et al., 1999, J. Parasitol. 85: 1072-1075), but not in a bovine model (Andrianarivo et al. 1999, Int. J. Parasitol. 30:985-990). Immunization with live vaccines, based on less virulent isolates, has been also used (Atkinson et al. 1999. Parasitology 118:363-370) or temperature-sensitive mutants (Lindsay et al. 1999. J. Parasitol. 85: 64-67), in vaccination tests in mice with the aim of stimulating a protective immune response against a fatal infection by *N. caninum*, obtaining encouraging but not definitive results, with the problem of originating persistently infected animals. On the other hand, the vaccines of subunits show a number of advantages over traditional vaccines (Jenkins, 2001. Vet. Parasitol. 101, 291-310), including the safety and relative stability of recombinant proteins, compared to live parasites, the flexibility of including only antigens inducing a protective immune response, and the ability to establish large-scale production. The development of subunit vaccines for the prevention of infection, abortion or vertical transmission of the infection, based on *N. caninum* antigens, provides a new tool for the control of the same. For the moment, very few studies have been performed on the matter. Only tachyzoite antigens or shared by both stages have been used, such as recombinant proteins expressed and purified from a prokaryote system, including NcMIC3, that induced protective immunity against cerebral neosporosis in a murine model (Cannas et al. 2003. J. Parasitol. 89(1), 44-50), as well as NcSAG1 and NcSRS2, two surface proteins of tachyzoite, inoculated in the same model combined as recombinant antigens and DNA vaccines (Cannas et al. 2003. Parasitology 126, 303-312), obtaining good results. Plasmids expressing NcGRA7 protein or NcsHSP33 protein have been recently used as DNA vaccines in a murine model, obtaining a partial protection against congenital transmission of the infection (Liddell et al. 2003. J. Parasitol. 89(3), 496-500). However, to date the development of these vaccines has not been based on specific antigens of the bradyzoite stage, because the first described in N. caninum is that produced by the gene NcSAG4 as shown in the description of the invention of this report.

As set out in the background, the isolation of genes expressed specifically in each stage is highly relevant for the study of this disease and the molecular mechanisms determining the establishment of the chronic infection, and the reactivation of the infection, improving the understanding and control of the disease. With this regard, the isolation of the NcSAG4 gene in N. caninum, homologous of the TgSAG4 gene, coding a specific protein of the bradyzoite stage in T. gondii, its cloning and the expression of stage specific antigen NcSAG4 as recombinant protein, as set out in the description of the invention hereof, provides a highly valuable solution for the diagnosis of neosporosis, and for the analysis of the pathogenesis of the disease, and its use as a vaccine is an alternative for the control of the same.

DESCRIPTION OF THE INVENTION

Use of the Gene NcSAG4 for the Diagnosis and Prevention of Neosporosis and as a Marker for Analysis of the Pathogenesis The aim of the invention is to provide a useful reagent for use in diagnostic and vaccination purposes against N. caninum. In addition, it provides a marker for the analysis of the pathogenesis of neosporosis, mainly for the study of the establishment of the chronic phase of the infection, and for the reactivation of the same. Therefore, a molecular technology is described, that has allowed for the identification, isolation and characterisation of the gene NcSAG4 of N. caninum, the first specific gene of the bradyzoite stage described in this parasite. For this, several DNA fragments of the gene NcSAG4 are amplified by PCR, using a combination of four degenerated oligonucleotides, designed on the basis of the sequence of amino acids of the protein TgSAG4 of T. gondii, one of which (SEQ ID NO: 1) is described by Ödberg-Ferragut et al. (1996, Mol. Biochem. Parasitol. 82, 237-244). The other three oligonucleotides designed were called SAG4-2, SAG4-3 and SAG4-4 and are identified in the list of sequences as SEQ ID NO: 2, SEQ ID NO: 3, and SEQ ID NO: 4, respectively. From the sequence obtained, another four oligonucleotides are designed to complete the sequence of the gene by the genome walking technique. Therefore, the oligonucleotides 1R5SAG4 (SEQ ID NO: 5) and 2R5SAG4 (SEQ ID NO: 6) were used to complete the gene in the 5' sense. The oligonucleotides 1F3SAG4 (SEQ ID NO: 7) and 2F3SAG4 (SEQ ID NO: 8) were used to complete the gene in 3' sense.

This invention describes a method of cloning of the NcSAG4 gene by amplification by PCR, using oligonucleotides specially designed for it and their subsequent digestion with restriction enzymes. This cloning is performed in two types of plasmids, pRSET and pcDNA3.1/His (both of Invitrogen), for the expression in a prokaryote and eukaryote system, respectively. A part of the NcSAG4 gene is inserted in plasmid pRSET, coding from amino acid 29 to 148, both included, corresponding to the sequence of mature protein NcSAG4, excluding the regions of the signal peptide of the amino terminus of the protein, and of possible signal peptide of the carboxy terminus thereof. For this, the corresponding region of gene NcSAG4 is amplified by PCR from genomic DNA of N. caninum, using the oligonucleotides designed for it, called F85NcSAG4 (SEQ ID NO: 13) and Re444NcSAG4 (SEQ ID NO: 14). In this system, recombinant protein pRNcSAG4 is expressed under the control of the RNA polymerase promoter of phage T7, as fusion protein, bound in its amino end to a tag of histidines that allows purification by affinity chromatography. To produce the recombinant protein pRNcSAG4, rosetta (DE3) pLysS cell strain from E. coli (Novagen) are used, that express on an induced basis the RNA polymerase of phage T7, by addition of IPTG to the culture medium, permitting the expression of recombinant proteins. The use of this recombinant protein for serologic diagnosis of neosporosis provides a highly valuable novel tool for the differential diagnosis of the different stages, acute and chronic, of the infection, by ELISA, radioimmunoassay (RIA) or any other method based on the antigenicity of these polypeptides, as shown in the development of this invention, by the Western blot technique described. Therefore, antibodies against the protein pRNcSAG4, separated by electrophoresis under denaturing conditions in 15% acrylamide-DATD gels, in sera from foetus and calves congenitally infected on nature by N. caninum, are detected. This suggests the value of this protein from both the viewpoint of differential diagnosis of acute and chronic infection by N. caninum and also from the viewpoint of the prevention, by its use as vaccine.

As with the development of monoclonal antibodies and polyclonal monospecific sera against recombinant protein pRNcSAG4, it is an alternative for the diagnosis by the development of a competition ELISA based on them. Furthermore, these monoclonal antibodies or specific polyclonal sera against the polypeptides described herein are used for the diagnosis of chronic infection by N. caninum in animal tissues by immunohistochemistry, immunofluorescence or any other method based on the detection of the parasite by said serum.

An objective of this invention is to provide vaccines against neosporosis, vertical transmission and establishment of chronic infection. The expression system of heterologous genes in prokaryotes offers the advantage of large-scale production of the recombinant antigen, using it as vaccine of subunits. These vaccines have another advantage, namely that they are used as labeled vaccines, and the immune response they produce can be easily distinguished from that caused by the parasite in infected animals, which is critical in programs for disease eradication. In addition, these vaccines are safe, which offers an advantage over the vaccines based on recombinant vectors such as viral ones. However, the latter offer the advantage of replication which allows for immunization with low doses.

Nevertheless, these types of recombinant proteins used as subunit vaccines induce an immune response mainly of humoral type. Therefore, to address the immune response also to a cell-based response, adjuvants aimed at this response are also used. On the other hand, to guide the cell-based response and assure the appropriate protein folding, DNA vaccines are used.

This invention describes a DNA vaccine based on NcSAG4 protein, that is used or not in combination with the recombinant protein pRNcSAG4, produced in the abovementioned prokaryote system. For this, the complete codifying region of the gene NcSAG4 is amplified by PCR by the use of oligonucleotides designed for that purpose, called FNcSAG4 (SEQ ID NO: 11) and ReNcSAG4 (SEQ ID NO: 12) and is inserted in an expression vector for mammal cells, the plasmid pcDNA3.1/His, at the sites of restriction Bam HI and Eco RI, obtaining the recombinant plasmid called pCDA10, that is used as DNA vaccine.

On the other hand, this invention describes the use of the gene NcSAG4 as marker of the bradyzoite phase of *N. caninum*, associated with chronic infection. This gene is used as marker by the use of the nucleotide molecules described herein for the diagnosis of chronic infection by *N. caninum* by PCR or RT-PCR, hybridization in situ with DNA probes, or any other detection method based on nucleic acids of the parasite from tissues or fluids of animals infected. A method of detection of expression of the gene NcSAG4 in the parasite, by RT-PCR, based on oligonucleotides designed for the isolation of the gene called 1 F3SAG4 (SEQ ID NO: 7) and 1R5SAG4 (SEQ ID NO: 5) is detailed. This RT-PCR allows the use of the NcSAG4 gene as a marker of stage conversion of *N. caninum*, in the intermediate host, and is a tool necessary for the analysis of the mechanisms determining the establishment of chronic infection and those involved in the reactivation of the infection, in animals persistently infected, and of factors influencing these conditions, and to establish the efficiency of vaccine products against *N. caninum*, in terms of protection against the establishment of chronic infection and reactivation. Furthermore, the use of the promoter of the gene NcSAG4 to express heterologous genes in *N. caninum* cells transfected thanks to gene constructions built with the above promoter, allows the analysis of molecular mechanisms determining the conversion of the tachyzoite to the bradyzoite stage and vice versa, both in expression systems in vitro and in vivo, in cell cultures or experimental animals.

DESCRIPTION OF DRAWINGS

To complement the description and in order to help for a better understanding of the characteristics of the invention, a set of drawings is enclosed to this descriptive report on an illustrative and non limiting basis, as an integral part thereof.

METHOD OF THE INVENTION

This invention is additionally illustrated by the following examples, which are not limitative of its scope, which is defined solely by the enclosed claiming note.

Example 1

Isolation and Characterisation of Gene NcSAG4

For the isolation of gene NcSAG4 of *N. caninum*, the method called genome walking was used, which allows the amplification by PCR fragments of DNA of unknown sequence, but flanking known DNA regions.

To amplify the known sequence, four degenerated oligonucleotides were used improving those described to clone the gene TgSAG4 of *T. gondii* (Ödberg-Ferragut et al., Mol. Biochem. Parasitol. 82 (1996) 237-244). One of the forward oligonucleotides used was oligo 1a (SEQ ID NO 1), described by these authors, and the other three were designed based on the amino acid sequences coded by the gene TgSAG4 of *T. gondii* present in the databases of the following strains: RH (AF340224.1), PLK (Z69373.1), Prugniaud (AF340225.1) and CEP (AF340226.1). Therefore, a forward oligonucleotide was designed, called SAG4-2 (SEQ ID NO: 2) and two reverse oligonucleotides called SAG-3 (SEQ ID NO: 3) and SAG4-4 (SEQ ID NO: 4).

To perform the PCR, 0.4 µg of genomic DNA, isolated from *N. caninum* tachyzoites, were used. For the isolation of genomic DNA, a commercial kit was used, following the instructions of use (GenomicPrep Cells and Tissue DNA Isolation kit, Amersham Biosciences). The positive control used was genomic DNA of *T. gondii* isolated by the same method. The DNA polymerase used was the enzyme EcoTaq (Ecogen) at 2.5 U per reaction, in the corresponding buffer, in the presence of $Cl_2Mg$ (4 mM), dNTPs (200 µM) and 40 pmol of each degenerated oligonucleotide. The PCR conditions were: 5 minutes of denaturalisation at 94° C., followed by 40 cycles of 1 minute at 94° C., 1 minute annealing where a temperature gradient was performed, from 43° C. to 56° C. (FIG. 1, lanes 4-9), 1 minute at 72° C., increasing the elongation one second every cycle, and finally an elongation of 10 minutes at 72° C. The negative control used was the mixture of a reaction without DNA (FIG. 1, lane 1) or genomic DNA from non-infected MARC-145 cells (FIG. 1, lanes 2 and 3).

Figure 1:
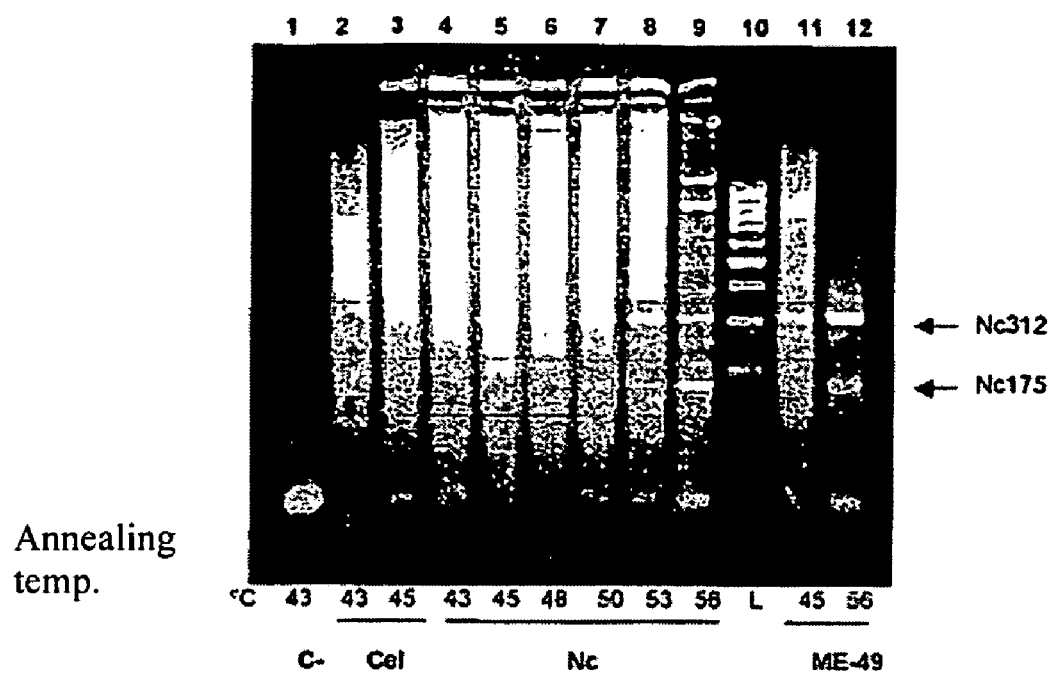
FIG. 1. It represents the amplification of sequences Nc175 and Nc312 of the genome of *N. caninum*, as explained in example 1 of this report.

As a result of the PCR, several fragments were amplified when using the melting temperature of 56° C., that were separated by electrophoresis in a 2% agarose gel in TBE at 1× (FIG. 1) both from genomic DNA of *N. caninum* (FIG. 1, lane 9) and *T. gondii* (FIG. 1, lane 12). From these fragments, two corresponded to the expected size for the combination of oligonucleotides 1a and SAG4-3 of 175 pb (Nc175), and 1a with SAG4-4 of 312 pb (Nc312). These DNA fragments were purified from a 2% agarose gel in TBE buffer 1×, using a commercial kit (GenomeGENECLEAN®Turbo nucleic acid purification kit, Q-BIOgene) following the indications of the manufacturer and sequenced with oligonucleotide 1a (Sequencing Service of the Institute of Biomedical Research "Alberto Sols", CSIC-UAM). The resulting nucleotide sequence was compared to those existing in the databases (BLASTN-nr, www.ncbi.nlm.nih.gob/blast) with a similarity of 82% with the sequence of gene TgSAG4 of three strains of *T. gondii* in 64 pb of the fragment. Furthermore, when translating the sequence Nc175 to the different possible open reading frames, and comparing it to the *T. gondii* database (TgGI: TIGR *Toxoplasma gondii* gene index, www.tigr.org/tdb/tgi/tggi), it evidenced a similarity of 68% with a group of sequences described as surface protein (TC2754), that is consistent with the proteins encoded by the sequences of gene TgSAG4 of the above strains (RH, PKL, Prugniaud and CEP) and with a EST described from a gene library of bradyzoites of the strain ME49 (Toxoplasma gondii v3, Parasite Consensus EST Data bases). Finally, the sequence Nc175 was compared to the database of *N. caninum* (NcGI: TIGR *Nespora caninum* gene index, www.tigr.org/tdb/tgi) and had no similarity with the sequences described to date.

Figure 2:
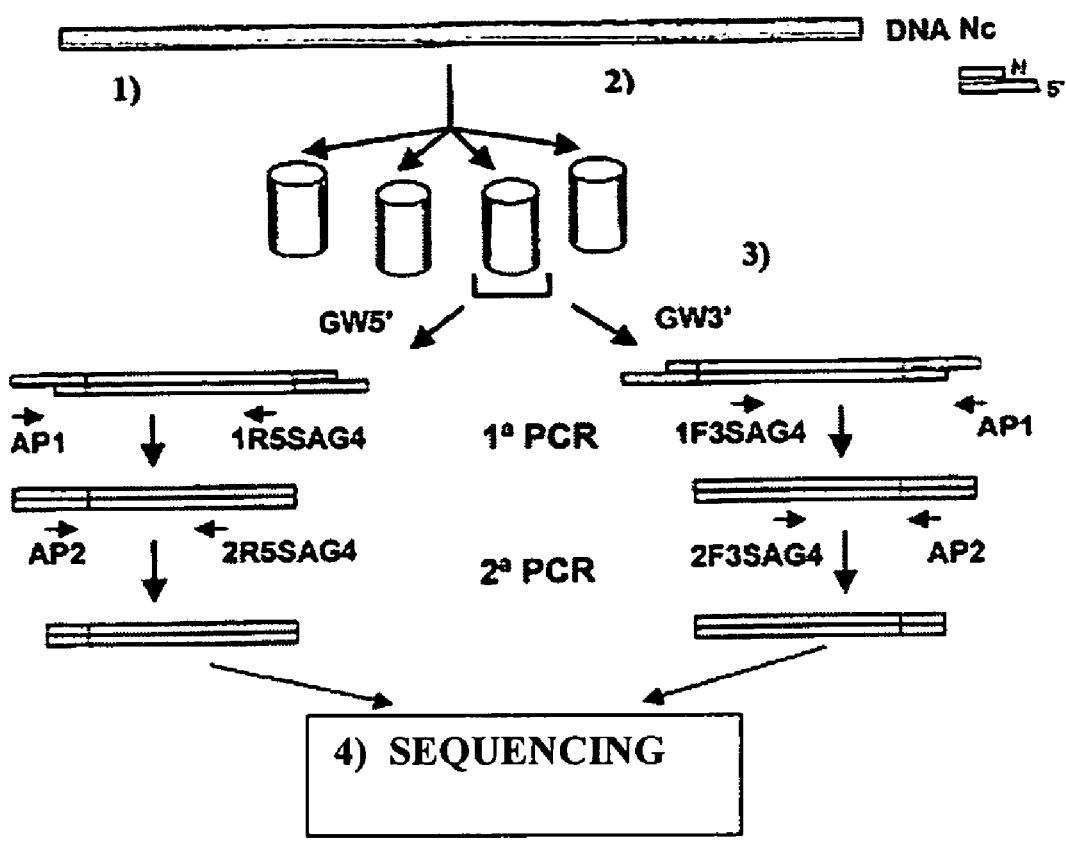
FIG. 2. It represents the scheme of the genome walking, as explained in example 1 of this report.

Once the sequence Nc175 was isolated, the gene NcSAG4 was identified using the genome walking method in 5' and 3' sense from the sequence Nc175, from the genomic DNA of *N. caninum*, using a commercial kit (Universal Genome Walker® kit, BD Biosciences Clontech). The first step to perform this technique is digestion (FIG. 2, step 1) of genomic DNA with four different restriction enzymes that produce blunt edges: EcoRB (1), DraI (2), PvuII (3) and StuI (4) and subsequent binding to adapters (FIG. 2, step 2), following the manufacturer's instructions. Then, with each gene library thus obtained, a double PCR is performed using the oligonucleotides binding to the adapter (AP1 and AP2) and the specific oligonucleotides of the gene, designed on the basis of the known genomic sequence (FIG. 2, step 3). The oligonucleotides designed from the sequence Nc175 for performing genome walking in the 5' sense were called 1R5SAG4 (SEQ ID NO: 5) and 2R5SAG4 (SEQ ID NO: 6) and those designed for performing genome walking in the 3' sense were called 1F3SAG3 (SEQ ID NO: 7) and 2F3SAG4 (SEQ ID NO: 8). The first PCR was performed with each genomic DNA gene library using oligonucleotides AP1 and 1R5SAG4 or 1F3SAG4 for performing the genome walking in the 5' or 3' sense respectively, following the instructions of the manufacturer, using a long-distance thermostable DNA polymerase (Advantage® Genomic PCR kit, BD Biosciences Clontech). The PCR conditions were 7 cycles of 25 seconds at 94° and 3 minutes at 68° C. followed by 32 cycles of 25 seconds at 94° C. and 3 minutes at 64° C., with a final elongation at 64° C. for 7 minutes. The second PCR was performed from a 1:50 dilution of the products of the first PCR and was performed with oligonucleotides AP2 and 2R5SAG4 or 2F3SAG4 for performing the genome walking in the 5' or 3' sense respectively. The conditions of the second PCR were: 5 cycles of 25 seconds at 94° C. and 6 minutes at 68° C., followed by 20 cycles of 25 seconds at 94° C. and 6 minutes at 64° C., with a final elongation at 64° C. for 10 minutes. The DNA fragments obtained by genome walking were purified as described above and sequenced (FIG. 2, step 4).

Therefore, with the comparison of the sequences of the different amplified fragments, a sequence of 601 nucleotides (SEQ ID NO: 9) could be established. This sequence was called NcSAG4, for its homology with that of gene TgSAG4 of *T. gondii*, which encodes a specific protein of the bradyzoite stage. Furthermore, the existence of an open reading frame (ORF) of 522 pb was verified, with a size similar to its homologue in *T. gondii*, encoding a protein of 173 amino acids (SEQ ID NO: 10). When comparing the sequence of amino acids coding this ORF to the sequences existing in the databases (BLASTx, www.ncbi.nlm.nih.gov/blast), a similarity of 69% was found with those of protein TgSAG4 of the different *T. gondii* strains.

Example 2

Expression of Antigen NcSAG4 as Recombinant Protein

Figure 3:
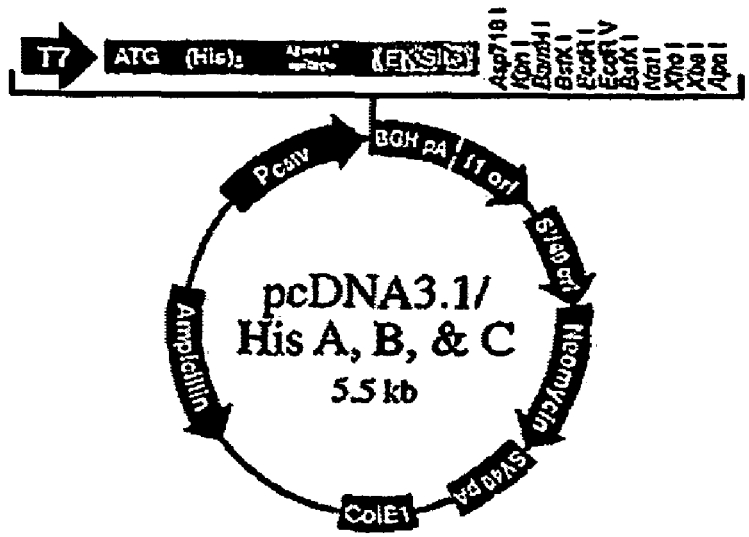
FIG. 3. It represents the insertion of the gene NcSAG4 in expression plasmids. Panel A. PcDNA3.1/His. Panel B: pRSET, as explained in example 2 of this report and the scheme of the recombinant protein, pRNcSAG4 (Panel C) as explained in example 2 of this report.
Figure 3:
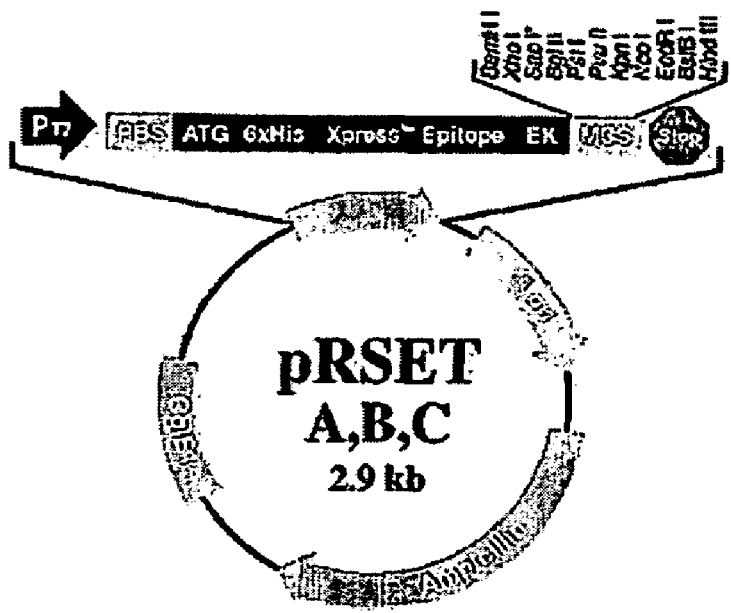
Figure 3:
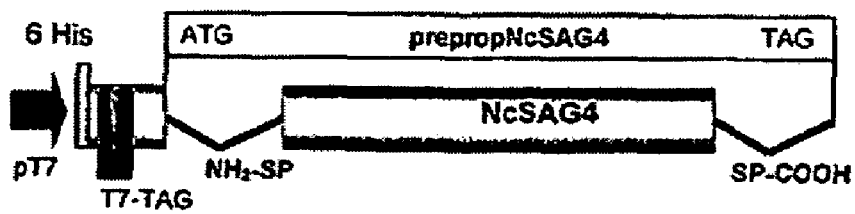

Once gene NcSAG4 was identified, the coding region was inserted in expression vectors to produce the antigen NcSAG4 as recombinant protein in a heterologous system. For the eukaryote system, the expression plasmid pcDNA3.1/His®-C (Invitrogen) was chosen (FIG. 3, panel A) and for the prokaryote system, the expression plasmid pRSET-C (Invitrogen) (FIG. 3, panel B). In plasmid pcDNA3.1/His©-C the complete coding region of gene NcSAG4 was inserted at the sites BamHI and EcoRI. For this, a PCR was performed from the genomic DNA of *N. caninum*, using oligonucleotides designed for it (OligoANALYZER 1.0.2.). The forward oligonucleotide was called FNcSAG4 (SEQ ID NO: 11), including in its 5' edge a specific site of recognition for BamHI, followed by a NcoI site, before an identical sequence to the 5' edge of ORF of gene NcSAG4. The reverse oligonucleotide was called ReNcSAG4 (SEQ ID NO: 12), including in its 5' edge a specific recognition site for EcoRI, followed by a complementary reverse sequence to the 3' edge for ORF of gene NcSAG4.

For the expression in prokaryotes, a part of gene NcSAG4 was inserted, that codes a truncated form of the protein, from amino acid 29 to 148, both included, at sites BamHI and EcoRI of the plasmid pRSET-C. For this, two oligonucleotides were designed using the software (OligoANALYZER 1.0.2.). The forward oligonucleotide was called F85NcSAG4 (SEQ ID NO: 13), including in its 5' edge a specific recognition site for BamHI, followed by an identical sequence of the ORF of gene NcSAG4 from nucleotide 83 to 100. The reverse nucleotide was called Re444NcSAG4 (SEQ ID NO: 14), inserting in its 5' edge a specific recognition site for The direct oligonucleotide was called F85NcSAG4 EcoRI, followed by a termination codon (TAA) and then the complementary reverse sequence of the ORF of gene NcSAG4, from nucleotide 328 to 444.

For performing the PCR in both cases, 0.1 µg of genomic DNA were used by reaction, isolated from *N. caninum* tachyzoites. The DNA polymerase used was EcoStart (Ecogen), 1.25 U per reaction, in a final volume of 25 µl in the corresponding buffer, in the presence of 2.5 mM of $Cl_2Mg$, dNTPs (200 µM) and 40 pmol of each oligonucleotide. The pCR conditions were 7 minutes of denaturalisation at 95° C., followed by 40 cycles of 30 seconds at 95° C., 1 minute at 53° C., 4 minutes at 72° C., increasing the elongation one second every cycle, and finally one elongation of 10 minutes at 72° C. The PCR products were viewed in a 1.5% agarose gel in TAE buffer 1×, stained with ethidium bromide (BrEt), observing a size of 542 pb, corresponding to that expected for the ORF of gene NcSAG4, and of 385 pb for the truncated gene. Then, these DNA fragments were purified and digested with the restriction enzymes BamHI (5 U) and EcoRI (6 U) in the appropriate buffer (buffer B, Roche) in a final volume of 50 µL, during four hours at 37° C. in a water bath. At the same time and under identical conditions, each plasmid vector was digested. These plasmids were treated at the end of digestion with 2 U of shrimp alkaline phosphatase (SAP) enzyme for 30 minutes in the same digestion reaction at 37° C. Then, the SAP enzyme was inactivated for 20 minutes at 65° C., in the presence of EDTA 10 mM. Once digestion was completed, both the plasmid DNA and the PCR products were viewed in an agarose gel of low melting point at 1.5% in TAE buffer 1× stained with BrEt and then purified from it.

For manipulation of plasmids, the method described by Sambrook et al. (1989) was basically followed. Once each digested DNA fragment was purified, it was ligated to 50 ng of the corresponding vector, with the pCDNA3.1/His©-C (Invitrogen) for the complete ORF of gene NcSAG4 and plasmid pRSET-C for the truncated gene, at a vector-insert 1:3 ratio, in the presence of 1 U of the enzyme T4DNA ligase, in the appropriate buffer and in a final volume of 15 µL. The ligation was made in 0.5 mL tubes (Multi™, Sorenson Bioscience) in a thermocycler for 18 hours at 12° C., and subsequently stored at −20° C. until used.

Figure 4:
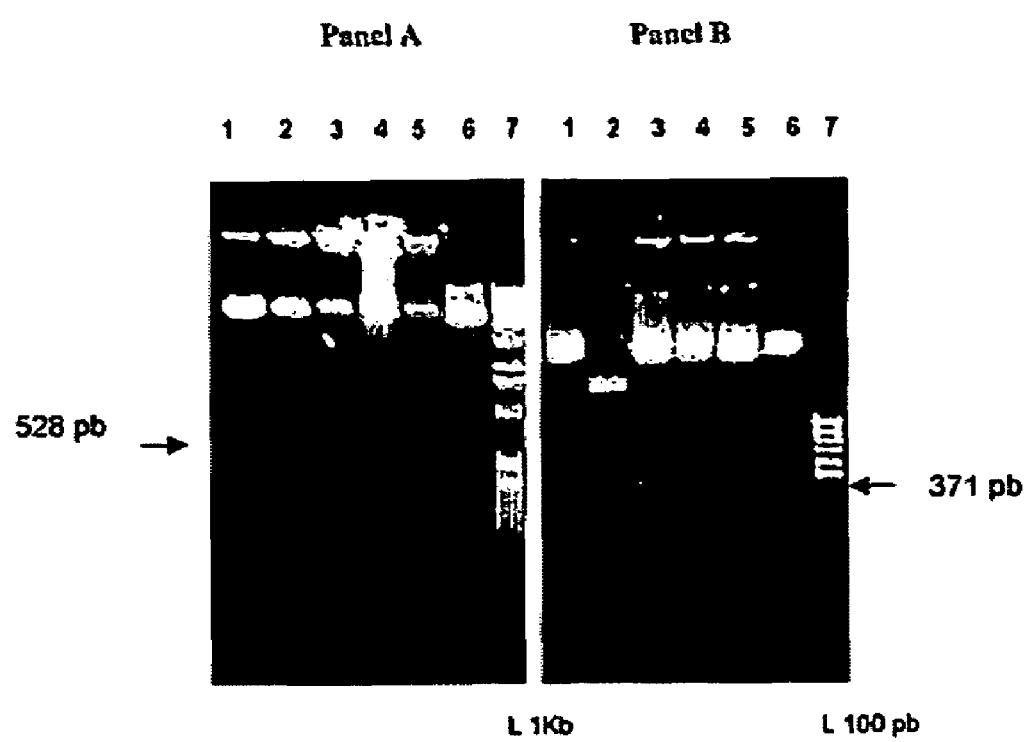
FIG. 4. The figure shows the selection of recombinant plasmids by digestion with restriction enzymes, as explained in example 2 of this report. Where WM is "molecular weight standards, low range (Bio-rad)".

Once ligation was performed, it was used to transform frozen competent cells of E-coli DH5α strain by electroporation. For transforming the bacteria by electroporation, the instructions of the manufacturer of the electroporator (GenePulser™, Bio-rad) were basically followed. Two mm electroporation trays (Equibio) previously chilled on ice were used. The competent bacteria were unfrozen and kept in ice until adding 5 µL of the ligation. After one minute in ice, they were subject to a pulse of 2.5 kV at 25 µFD and 200 Ohm, for 4-5 seconds. The transformed bacteria were immediately resuspended in 500 µL of SOC medium (MgSO$_4$ 10 mM, MgCl$_2$ 10 mM and glucose 20 mM added to SOB medium: bactotryptone 2%, yeast extract 0.5%, NaCl 10 mM and KCl 2.5 mM) and grown for one hour at 37° C. and then 200 µL of a cell suspension were plated in LB-agar medium (1.5% noble gar) in the presence of 100 µg/mL of ampicillin, antibiotic against which the plasmids used were resistant. The transformed bacteria with the plasmids were selected after growth in plaques with the appropriate medium for 18 hours at 37° C. Ten clones of each were selected and grown overnight at 37° C. in 3 mL of liquid LB medium with 100 µg/ of ampicillin for subsequent isolation of plasmid DNA. This DNA was obtained by the alkaline lysis method and subsequently viewed in a 0.8% agarose gel in TAE buffer 1× for selecting clones with the plasmid of the expected size. The relevant plasmids were called pCDA, numbered from 1 to 10 according to the clone, to the plasmid built by insertion of the complete ORF of the gene NcSAG4 in plasmid pcDNA3.1/His/©-C, with an expected size of 6,028 pb. The plasmid obtained by insertion of the truncated form of gene NcSAG4 of nucleotide 83 to 444 in pRSET-C (3,235 pb) was called pRC, from 1 to 10, depending on the clone. Based on the size observed, four clones were chosen from each for characterisation by restriction enzymes (FIG. 4). Therefore, the plasmids obtained were digested with the restriction enzymes BamHI (5 U) and EcoRI (6 U) in the appropriate buffer (buffer B, Roche) in a final volume of 20 µL for two hours at 37° C. in a water bath. The digested plasmid DNA was separated in a 0.8% agarose gel in 0.5% TBE buffer, observing the release of a fragment of the appropriate size in each plasmid built. Therefore, the plasmids pCDA5, pCDA6, pCDA9 and pCDA10 released a fragment of 528 pb (FIG. 4, panel A, lanes 1 to 4 respectively), and the fragment of 371 pb in plasmids pRC6, pRC7, pRC9 and pRC10 (FIG. 4, panel B, lanes 3 to 6 respectively), In addition, vectors pcDNA3.1/His©-C (FIG. 4, panel A, lanes 5 and 6) and pRSET-C (FIG. 4, panel B, lane 1) were cut and used as controls of digestion. In the agarose gel the non-digested plasmid pRSET-C (FIG. 4, panel B, lane 2) was also loaded. Plasmids pCDA10 and pRC10 were sequenced using the commercial oligonucleotide T7, confirming the insertion of the fragments in the expression vectors adequately.

The recombinant protein pRNcSAG4 (SEQ ID NO: 15) covers from amino acid 29 to 148, encoded by the ORF of gene NcSAG4, described herein and corresponds to the amino acid sequence of the possible mature protein NcSAG4, lacking the signal peptide of the amino terminus and the possible signal peptide of the carboxy terminus, following the criteria revised by Gerber et al. (1992. JBC 267. 12168-12173) bound in the amino terminus to a tag of amino acids including 6 histidines, which allows purification by affinity chromatography, peptide T7-tag and an enterokinase recognition area. FIG. 3, panel C, shows a chart of recombinant protein pRNcSAG4.

To express the recombinant protein in the prokaryote system, Rosetta (DE3)pLysS cell strain of E. coli (Novagen) were transformed with the plasmid pRC10, following the indications of the manufacturer. The transformed cells with plasmid pRC10 were plated in LB-agar medium with ampicillin (100 µg/mL) and chloramphenicol (34 µg/mL) and grown overnight at 37° C. The day after six colonies of the plaques were selected and grown overnight at 37° C. in 3 mL of the same selection liquid medium. The day after the culture was diluted 1:10 in the same growth medium and kept under identical conditions until reaching A$_{600}$ of 0.9 OD. Then expression of the recombinant protein was induced in the presence of 1 mM IPTG for 4 hours under stirring at 250 rpm and 37° C. Finally, the cells were collected by centrifugation at 3,500×g for 15 minutes. Once the supernatant was removed, the sediments were stored at −80° C. until use.

Figure 5:
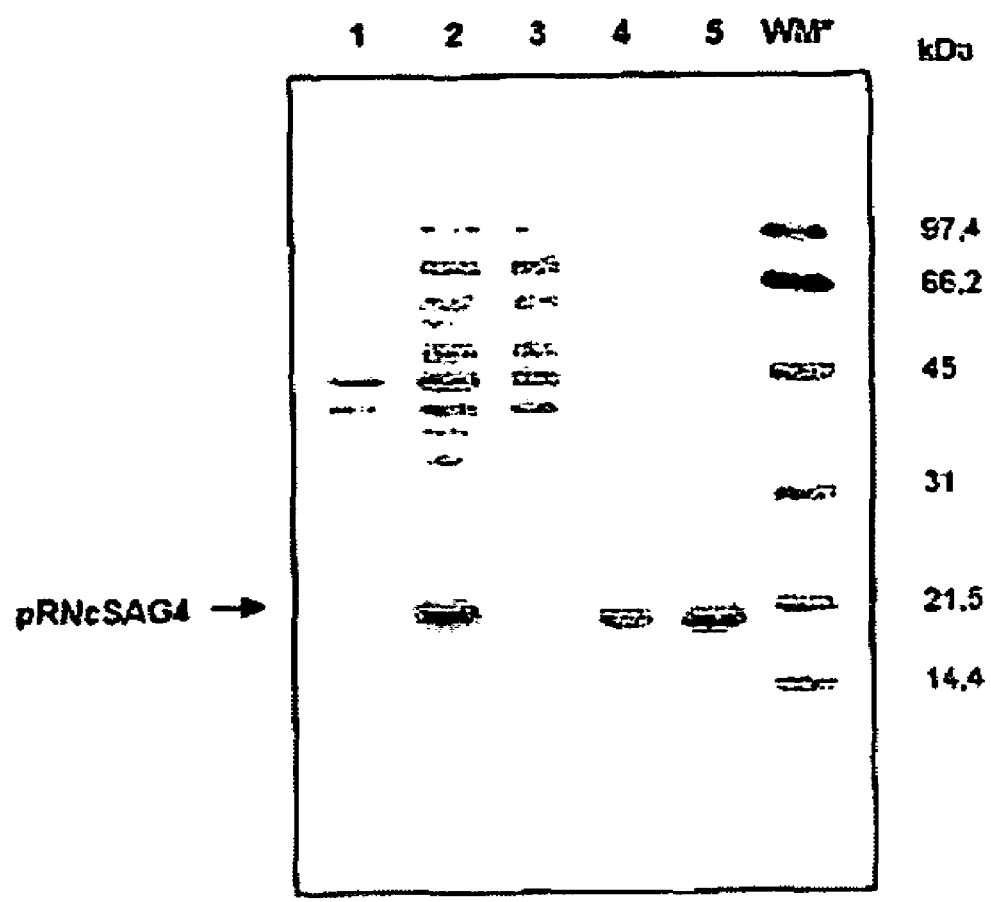
FIG. 5. Expression of recombinant protein pRNcSAG4 in *E. coli* as explained in example 2 of this report.

For the characterisation of the expression of recombinant proteins, cell sediments previously collected were lysed in a commercial lysis solution called BugBuster (Novagen) at 1× in Tris 20 mM pH 7.98 at a concentration of 5 mL/g of cell sediment. They were incubated under gentle stirring and room temperature in the presence of the enzyme Benzonase (Novagen, IU/mL of Bugbuster 1×) for 40 min. Then the soluble fraction was separated from the sediment, where the inclusion bodies are located, by centrifugation at 20,000×g for 15 minutes for establishing the location of the relevant protein. The inclusion bodies were then washed according to the indications of the manufacturer. Finally, the proteins were separated, solubilised in loading buffer Laemmli 1× (Laemmli 1970. Nature 227, 680-685), at a percentage of 50 uL/mL of original culture, by electrophoresis under denaturalising conditions in 15% acrylamide/DADT gels (FIG. 5). The proteins were separated from both a total extract of bacteria collected before induction (FIG. 5, lane 1) and after induction (FIG. 5, lane 2) and the supernatant (FIG. 5, lane 3) and the sediment, collected previously (FIG. 5, lane 4), and also the inclusion bodies after washings (FIG. 5, lane 5). Therefore, the expression of recombinant protein pRNcSAG4 in Rosetta (DE3)pLysS of E. coli (Novagen) was confirmed, with the expected apparent molecular mass of 17.2 kDa and its location in inclusion bodies.

Example 3

Determination of Immunogenicity of Protein pRNcSAG4

Figure 6:
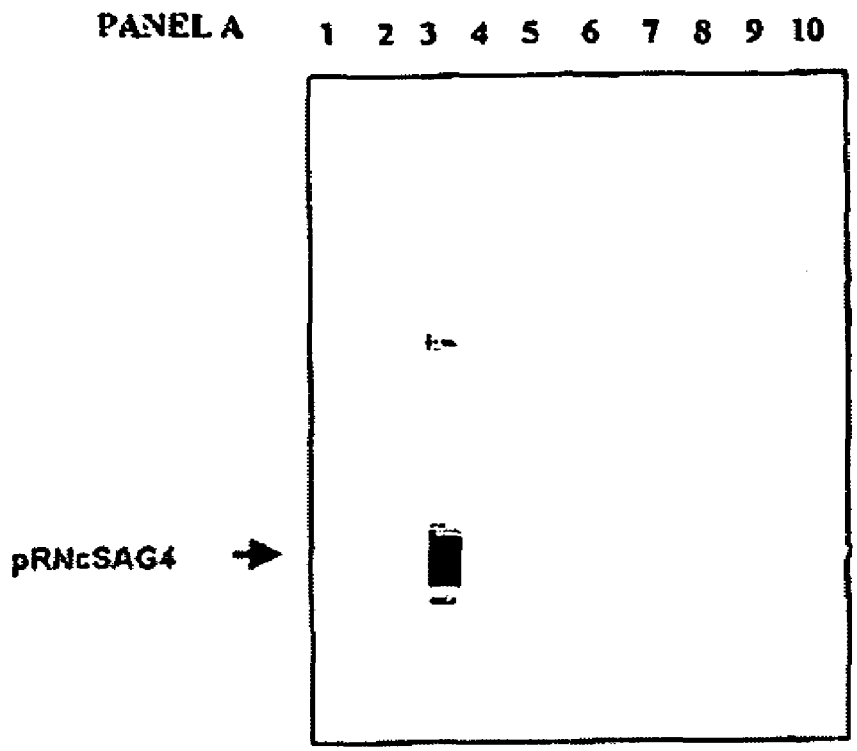
FIG. 6. Characterisation of immunogenicity of recombinant protein pRNcSAG4, as explained in example 3 of this report.
Figure 6:
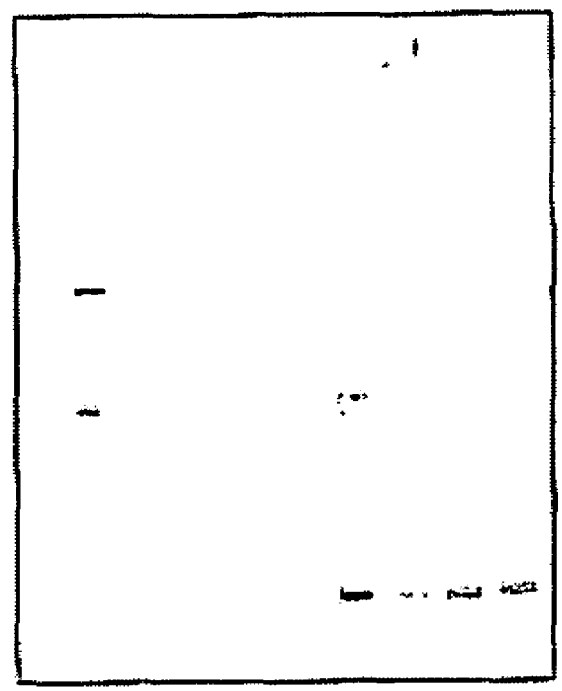

The immunogenicity of recombinant protein pRNcSAG4 was determined by Western blot (FIG. 6) using sera of bovine origin from animals naturally infected by N. caninum. The infection of these sera had been previously diagnosed by the ELISA technique and indirect immunofluorescence (IFAT), with high specific antibody titres. Three washings were performed of the inclusion bodies where protein pRNcSAG4 is located, using a 0.1× BugBuster solution, as instructed by the manufacturer. The proteins were then separated in 15% acrylamide-DATD gels by electrophoresis under denaturalising conditions, and finally electrotransfer was performed to a 0.2 µm nitrocellulose membrane (Bio.rad), at 400 mA for one hour sank in transfer buffer previously cooled (Tris 25 mM, glycine 192 mM pH 8.5 and 20% methanol). The bovine sera used were from different sources. In that sense, sera were from animals in which chronic infection was likely to be establishing, and where bradyzoites were developing such as those from animals born with congenital infection, which show precolostral seropositivity, or body fluids from foetuses aborted during the last term of pregnancy. On the other hand, sera from aborting cows were used, representing a possible reactivation of infection by *N. caninum*, that leads to abortion. Moreover, precolostral sera of three calves were used (FIG. 6, panels A and B, lanes 1, 2 and 3), with high titres against *N. caninum* by IFAT. Furthermore, abdominal fluid was used, with high antibody titre against *N. caninum* by IFAT, from foetuses aborted during the second (FIG. 6, panels A and B, lane 4) and third quarter of pregnancy (FIG. 6, panels A and B, lanes 5 and 6), from cows that had aborted, seropositive for *N. caninum* (FIG. 6, panels A and B, lanes 7 and 8). Finally, the serum from two other cows that had aborted was used (FIG. 6, panels A and B, lanes 9 and 10), seropositive to *N. caninum* by IFAT, with a high antibody titre.

As a control of the technique, Western blot was performed in parallel with the same sera, in a membrane where a soluble extract from *N. caninum* tachyzoites produced in vitro was transferred, using the same sera. To produce the soluble extract and for performing the Western blot, the above mentioned protocol was basically followed (Alvarez et al. 2002. Vet. Parasitol. 107, 17-27). The membranes were blocked with 3% BSA in TBS with 0.05% Tween-20 (TBS-T) stirring for one hour at room temperature. Then the membranes were incubated with sera of bovine origin, at a 1:20 dilution in TBS-T with 0.3% BSA for two hours under stirring at 37° C. After three fast washings with TBS-T, followed by one of 15 minutes and two of 5 minutes, the membranes were incubated with a mouse monoclonal antibody of anti bovine –IgG conjugated with peroxidase (Hipra) at a dilution 1:200 in TBS-T with 0.3% BSA for one hour under stirring at 37° C. After another series of washings under the above conditions, it was developed with a solution of substrate prepared immediately before use (60 mg of 4-chloro-1-naphtol dissolved in 20 mL of methanol, 100 mL of TBS and 0.060 mL of hydrogen peroxide), for 15 minutes at room temperature in darkness and under stirring.

By Western blot a clear response was detected against the recombinant protein in precolostral sera from calves infected congenitally by *N. caninum* (FIG. 6, panel A, lanes 1, 2 and 3) and in abdominal fluid of a fetus aborted in the last third of pregnancy (FIG. 6, panel A, lane 6). These animals had a clear response to immunodominant antigens of the tachyzoite stage (FIG. 6, panel B, lanes 1-3 and 6), except for two of the fetuses aborted (FIG. 6, panel B, lanes 4 and 5). However, no clear response was detected in cows that had aborted (FIG. 6, panel A, lanes 7-10) where however there was a clear response against immunodominant antigens of the tachyzoite stage (FIG. 6, panel B, lanes 7-10).

These results confirm the existence of a response against protein NcSAG4 in the animal naturally infected, in those cases where the chronic form of the infection may be establishing, that is, cases where transformation from tachyzoite to the bradyzoite occurs, confirming the specificity of protein NcSAG4 of this slow growth phase of the parasite, as with its homologous in *T. gondii* (TgSAG4). The lack of response against pRNcSAG4 in animals with acute infection, where the tachyzoite stage is characteristic, that however show a clear response against the tachyzoite extract, confirms again the specificity of protein NcSAG4 of the bradyzoite stage.

Example 4

Determination of the Transcription of the NcSAG4 Gene in the Bradyzoite Phase of *N. caninum* by RT-PCR To establish the stage specificity of the transcription of NcSAG4 gene of *N. caninum*, an RT-PCR performed from total RNA extracted from bradyzoites cultured in vitro has been developed. For the production of bradyzoites in cell cultures, the method described by Risco-Castillo et al. (2003) J. Parasitol, submitted for publication) was followed. For this, tachyzoites of *N. caninum* were used (Barber et al. 1995. Parasitol. 111, 563-568) to infect monolayers of MARC-145 cells (Kim et al. 1993. Arch. Virol. 133, 477-483) at a host-parasite ratio of 2:1. The infected cell cultures were kept in DMEM supplemented with 10% bovine fetal serum in the presence of Hepes (pH 7.2) 15 mM, glutamine (2 mM), penicillin (10 U/mL), streptomycin (10 µg/mL), fungizone (25 ng/mL) and incubated at 37° C. and 5% $CO_2$.

To induce stage conversion, the infected cultures were treated with sodium nitroprusiate (SNP) at a concentration of 70 µM in culture medium for 7 days after infection, and was replaced every two days. As a negative control, the infected cultures untreated with SNP were maintained, for the production of tachyzoites. A mixture of tachyzoites and bradyzoites was collected by scraping the infected cell monolayer and treated with SNP, centrifuging at 1350×g for 15 min at 4° C. The tachyzoites produced in the infected cultures untreated with SNP were collected by the same procedure. After two washings in PBS under the same conditions, the zoites were resuspended using a 25 G needle and purified using sephadex™ columns (PD-10, Amersham Biosciences) to remove cell debris. For this, after balancing the column with 5 mL of PBS, the suspension of zoites was allowed to flow by gravity in 5 mL of PBS. After two washings with the same volume of PBS, the zoites were collected by centrifugation at 1350×g for 15 min at 4° C. The zoites collected were kept frozen at –80° C. until used.

For extraction of total RNA, sediments of $10^7$ tachyzoites or a mixture of tachyzoites and bradyzoites were used, produced as above described. For this, the commercial kit NucleoSpin RNA II (BD Biosciences Clontech) was used, following the instructions of the manufacturer. The total RNA obtained was separated by electrophoresis in a 0.8% agarose gel in TAE1× buffer, for checking its quality.

Figure 7:
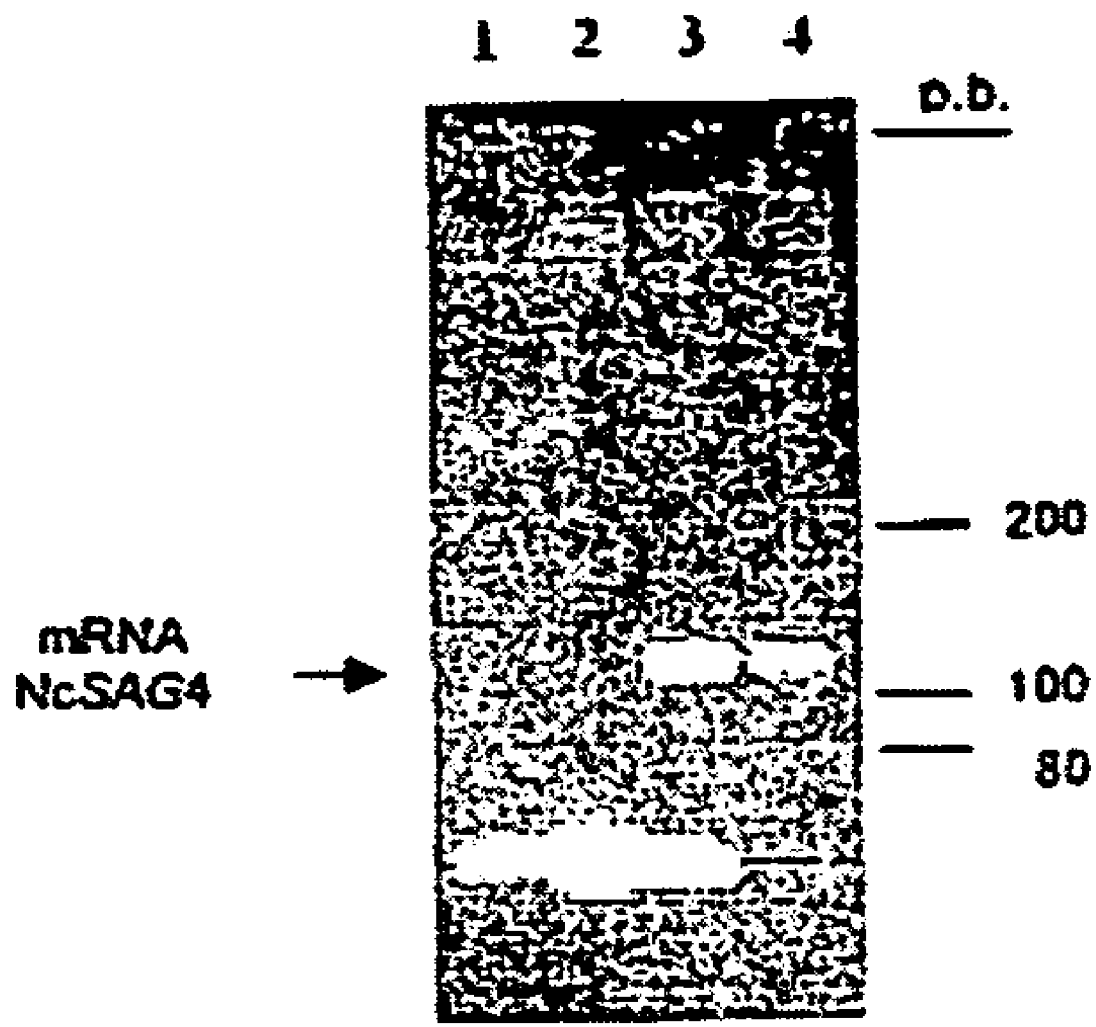
FIG. 7. Detection of the transcription of gene NcSAG4 in the bradyzoite stage of *N. caninum* by RT-PCR, as explained in example 4 of this report.

To perform the RT-PCR in a single tube, 100 ng of the total RNA of each origin, tachyzoite or bradyzoite, were used, and a commercial kit called "Quiagen® One-step RT-PCR kit" (Qiagen) was used, following the indications of the manufacturer (FIG. 7). For this, the oligonucleotides called IR5SAG4 (SEQ ID NO: 5) and 1 F3SAG4 (SEQ ID NO: 7) were used. The RT was performed at 50° C. for 30 minutes. The PCR conditions were 15 minutes of denaturalisation at 95° C., followed by 40 cycles of 30 seconds at 94° C., 1 minute at 61° C., 1 minute at 72° C., and finally an elongation of 10 minutes at 72° C. The PCR products were viewed in a 3% high resolution agarose gel in TBE buffer 0.5× stained with ethidium bromide (BrEt). As a result of the RT-PCR, the absence of transcription of RNA messenger (mRNA) of NcSAG4 in tachyzoites (FIG. 7, lane 2) and the presence of the above mRNA in the bradyzoites (FIG. 7, lane 3) were confirmed. As a positive control of PCR, 100 ng of genomic DNA obtained from *N. caninum* tachyzoites were used (FIG. 7, lane 4) and as negative control of PCR ultrapure water was used, instead of sample (FIG. 7, lane 1). This confirms the specificity of transcription of the NcSAG4 gene, of the bradyzoite stage of *N. caninum*, as with its homologous TgSAG4 of *T. gondii*.

The invention claimed is:

1. An isolated polypeptide selected from antigenic protein NcSAG4 of *N. caninum*, comprising SEQ ID NO: 10 or recombinant protein comprising SEQ ID NO: 10.

2. An immunogenic composition comprising an isolated polypeptide of claim 1.

3. The immunogenic composition according to claim 2, further comprising an adjuvant or a cytokine.

4. A method of preparing of an immunogenic composition comprising combining an isolated polypeptide of claim 1 with an adjuvant or a cytokine.

5. A kit for eliciting an immune response in mammals against neosporosis encompassing a container including an immunogenic composition of claim 2.

6. An isolated polypeptide comprising amino acids 29-148 of SEQ ID NO: 10.

* * * * *